(12) United States Patent  
Suzuki et al.

(10) Patent No.: US 8,912,384 B2  
(45) Date of Patent: Dec. 16, 2014

(54) ABSORBENT ARTICLE AND MANUFACTURING APPARATUS FOR ABSORBENT ARTICLE

(75) Inventors: Nahomi Suzuki, Kagawa (JP); Tatsuya Tamura, Kagawa (JP); Nobuyuki Kato, Kagawa (JP)

(73) Assignee: Unicharm Corporation, Ehime-Ken (JP)

( * ) Notice: Subject to any disclaimer, the term of this patent is extended or adjusted under 35 U.S.C. 154(b) by 446 days.

(21) Appl. No.: 13/497,870

(22) PCT Filed: Sep. 30, 2010

(86) PCT No.: PCT/JP2010/005906  
§ 371 (c)(1),  
(2), (4) Date: Jul. 11, 2012

(87) PCT Pub. No.: WO2011/040043  
PCT Pub. Date: Apr. 7, 2011

(65) Prior Publication Data  
US 2012/0271268 A1    Oct. 25, 2012

(30) Foreign Application Priority Data  
Sep. 30, 2009  (JP) ................................ 2009-229093

(51) Int. Cl.  
*A61F 13/15*    (2006.01)  
(Continued)

(52) U.S. Cl.  
CPC ..... *A61F 13/4756* (2013.01); *A61F 2013/4587* (2013.01); *A61F 13/536* (2013.01);  
(Continued)

(58) Field of Classification Search  
CPC ............... A61F 13/15707; A61F 13/15731; A61F 13/15723; A61F 13/15821; A61F 13/4704; A61F 13/47272; A61F 13/475; A61F 13/4756; A61F 13/533; A61F 13/536; A61F 2013/4587; A61F 2013/530927; A61F 2013/530934; A61F 2013/530941; A61F 13/53778

USPC .................................................. 604/379, 380  
See application file for complete search history.

(56) References Cited

U.S. PATENT DOCUMENTS 2,896,618 A  *  7/1959  Schaefer .......................... 602/47  
5,795,344 A  *  8/1998  Chappell ....................... 604/379  
(Continued)

FOREIGN PATENT DOCUMENTS

CN    1203069 A    12/1998  
JP    1099372 A    4/1998  
(Continued)

OTHER PUBLICATIONS

Office Action dated Sep. 2, 2013, corresponds to Chinese patent application No. 201080043718.9.

(Continued)

*Primary Examiner* — Lynne Anderson  
(74) *Attorney, Agent, or Firm* — Lowe Hauptman & Ham LLP

(57) ABSTRACT

A compressed portion is formed in the absorbent article by compressing the absorber through a compression process. The compressed portion has a top-surface groove formed on the skin-contact-surface side, and a back-surface groove formed on the clothing-contact-surface side. A bottom portion of the top-surface groove is flat. Since the recessed portions are formed in the bottom portion of the back-surface groove through the compression process, a compression part where the density of the absorber is increased more than in an uncompressed portion and high compression parts where the density of the absorber is increased more than in the compression part are formed in the bottom portion. Thus, the absorbent article can be permeate into by a thick liquid, and is more likely to absorb liquid.

10 Claims, 6 Drawing Sheets

(51) Int. Cl.
*A61F 13/475* (2006.01)
*A61F 13/536* (2006.01)
*A61F 13/533* (2006.01)
*A61F 13/47* (2006.01)
*A61F 13/45* (2006.01)
*A61F 13/53* (2006.01)

(52) U.S. Cl.
CPC .. *A61F 13/533* (2013.01); *A61F 2013/530941* (2013.01); *A61F 2013/530934* (2013.01); *A61F 13/4704* (2013.01); *A61F 13/15707* (2013.01)
USPC .......................................... 604/379; 604/380

(56) References Cited

U.S. PATENT DOCUMENTS

| | | | | |
|---|---|---|---|---|
| 5,941,861 | A | * | 8/1999 | Ng .............................. 604/366 |
| 6,159,190 | A | * | 12/2000 | Tanaka et al. ............ 604/385.24 |
| 2002/0065499 | A1 | | 5/2002 | Ohashi et al. |
| 2004/0253892 | A1 | * | 12/2004 | Baker et al. .................... 442/327 |
| 2006/0116653 | A1 | * | 6/2006 | Munakata et al. ............ 604/380 |
| 2008/0119810 | A1 | * | 5/2008 | Kuroda et al. ................ 604/379 |

FOREIGN PATENT DOCUMENTS

| | | |
|---|---|---|
| JP | 10099372 A | 4/1998 |
| JP | 10155832 A | 6/1998 |
| JP | 10272152 A | 10/1998 |
| JP | 10328232 A | 12/1998 |
| JP | 2002165835 A | 6/2002 |
| JP | 2007037677 A | 2/2007 |

OTHER PUBLICATIONS

Office Action issued Jul. 3, 2014, corresponds to Egyptian patent application No. PCT 589/2012.
International Search Report and Written Opinion for PCT/JP20101005906 dated Jan. 11, 2011.

* cited by examiner

US 8,912,384 B2

ABSORBENT ARTICLE AND MANUFACTURING APPARATUS FOR ABSORBENT ARTICLE

RELATED APPLICATIONS

The present application is a National Phase of International Application Number PCT/JP2010/005906, filed Sep. 30, 2010, and claims priority from, Japanese Application Number 2009-229093, filed Sep. 30, 2009.

TECHNICAL FIELD

The present invention relates to an absorbent article in which a groove is formed in a predetermined area of a topsheet.

BACKGROUND ART

For the purpose of liquid leak prevention or wear comfort improvement of an absorbent article such as a sanitary napkin, provision of a groove to a skin-contact surface of the absorbent article has been proposed (see Patent Literature 1). In an absorbent article disclosed in Patent Literature 1, small grooves are formed in a bottom portion of a groove, the small grooves being depressed further from the bottom portion of the groove. Since the groove is formed by a compression process, an absorber has a higher density at a portion between the bottom portion of the groove and a backsheet than at a portion where the groove is not formed. Further, the absorber has a higher density at a portion between a bottom portion of each small groove and the backsheet than at a portion between the bottom portion of the groove and the backsheet It is generally known that an absorber has higher absorbability at a portion with a high density than at a portion with a low density. For this reason, in the absorbent article described in Patent Literature 1, the grooves can absorb body fluid and can thus block flow of the body fluid. Further, since the absorbent article is easily bendable along the grooves, a wearer can enjoy better wear comfort. Note that high absorbability means a high absorbing speed here.

CITATION LIST

Patent Literature

PTL 1: Japanese Patent Application Publication No. Hei 10-155832 (e.g., FIG. 3)

The absorbent article of Patent Literature 1, however, has the following problem. It is conceivable that the absorbability of the absorber can be enhanced by enlarging the area of the high density portion in the absorber. However, excessive compression in forming the groove in a topsheet and the absorber by the compression process or the like increases strain on the topsheet at borders of the groove. This leads to a problem that the topsheet is easily torn along the groove. To lessen such strain, Patent Literature 1 employs a structure in which the small grooves are formed in the bottom portion of the groove to increase the density of the absorber in a stepwise manner.

Actual body fluid is a mixture of liquids of different viscosities. For example, a liquid with a high viscosity, or a thick liquid, has higher surface tension than a liquid with a low viscosity, or a thin liquid. For this reason, the thick liquid needs a longer time to reach the bottom portions of the small grooves than the thin liquid. As a result, while the thick liquid is clogging the bottom portion of the groove and the bottom portions of the small grooves, the thin liquid often spreads over the grooves clogged with the thick liquid, and leaks out of the absorbent article.

SUMMARY OF INVENTION

In this regard, the present invention has an objective to provide an absorbent article in which a groove is formed in an absorbing surface and which is capable of preventing breakage of the absorbing surface, and providing improved absorbability for a liquid with a high viscosity to prevent a liquid leak.

To solve the above-described problem, the present invention provides in a first aspect provides an absorbent article comprising: a liquid permeable topsheet; a liquid impermeable sheet; an absorber interposed between the topsheet and the liquid impermeable sheet and configured to absorb liquid; a top-surface groove formed in a predetermined area of the top surface in which the topsheet and the absorber are depressed towards a clothing-contact-surface side; and a back-surface groove formed in the clothing-contact-surface side in register with the top-surface groove in which at least the absorber is depressed towards a skin-contact-surface side, wherein in a widthwise cross section of the absorbent article, a recessed portion is formed in a bottom portion of the back-surface groove, the recessed portion recessed from the bottom portion of the back-surface groove towards the skin-contact-surface side, and the absorber has a higher density at a portion between the bottom portion of the top-surface groove and the recessed portion of the back-surface groove than at a portion between the bottom portion of the top-surface groove and the bottom portion of the back-surface groove.

In accordance with a second aspect, the invention provides a manufacturing apparatus for an absorbent article including a liquid permeable topsheet, a liquid impermeable sheet, and an absorber interposed between the topsheet and the liquid impermeable sheet and configured to absorb liquid, the manufacturing apparatus being configured to form a groove in a predetermined area of the topsheet of the absorbent article, and comprising: a first roll configured to rotate in a machine direction which is a direction of flow of steps for manufacturing the absorbent article, while being in contact with an intermediate continuum obtained by stacking the absorber on a continuum of the topsheet; a second roll placed facing the first roll with the intermediate continuum in between and configured to rotate in the machine direction, wherein a top-surface-groove die is formed on a surface of the first roll, the top-surface-groove die being configured to form a top-surface groove in a predetermined area of the intermediate continuum, the top-surface groove being depressed from the topsheet, a back surface groove die, and a plurality of back-surface-groove bump portions are formed on a surface of the second roll in an area including a region facing the top-surface-groove die, the back-surface-groove bump portions being configured to form a back surface groove depressed toward the topsheet in an area of the intermediate continuum on a side having the liquid impermeable sheet, the area corresponding to the top-surface groove.

The present invention can provide an absorbent article in which a groove is formed in an absorbing top surface is resistant to breakage of the absorbing surface, and provides improved absorbability for a liquid with a high viscosity to prevent a liquid leak.

DESCRIPTION OF EMBODIMENTS

Figure 1:
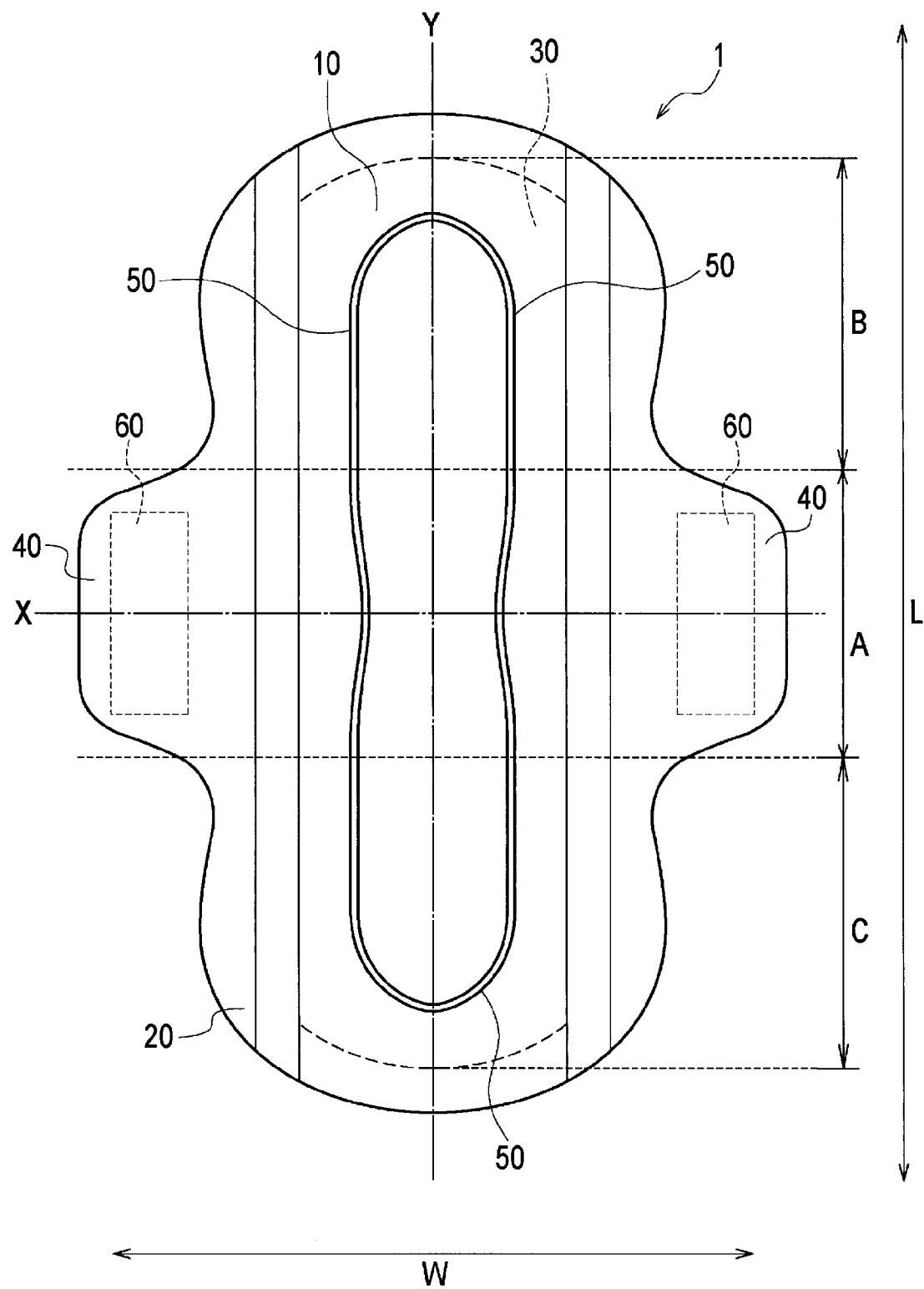
FIG. 1 is a plan view of an absorbent article according to an embodiment of the present invention, seen from a wearer's skin contact side.

An embodiment of an absorbent article according to the present invention is described, by way of example only, with reference to the drawings. Note that, in the following description of the drawings, the same or similar reference numerals denote the same or similar portions. In addition, it should be noted that the drawings are schematic and ratios of dimensions and the like are different from actual ones. Therefore, specific dimensions and the like should be determined in consideration of the following description. Moreover, it is a matter of course that the drawings also include portions having different dimensional relationships and ratios from each other.

The absorbent article 1 of FIG. 1 is in the form of a sanitary napkin. However, the features herein below described, consider both together and in isolation may have application to other types of absorbent articles, such as diapers and incontinence devices. The absorbent article of FIG. 1 includes: a liquid permeable topsheet 10, a liquid impermeable backsheet 20, an absorber 30 interposed between the topsheet 10 and the backsheet 20, and wing portions 40 which may be formed of a nonwoven fabric and which protrude outward from both edge portions of the absorbent article 1. Further, the absorbent article 1 has a centre area A, a front area B, and a back area C disposed along a longitudinal direction L. The front area B and the back area C are positioned outside of the centre area A in the longitudinal direction L.

The topsheet 10 may be a nonwoven fabric. The material of the topsheet 10 is not particularly limited as long as it is a sheet-like material having a liquid permeable structure, such as a woven fabric or a perforated plastic sheet. Any of natural fibers and chemical fibers can be used as the material for the woven fabric and the nonwoven fabric. In the present embodiment, only the topsheet 10 is placed on the skin side of the absorber 30, but there could be one or more intermediate layers.

Examples of the natural fibers include cellulose such as ground pulp, or cotton. Examples of the chemical fibers include regenerated cellulose such as rayon or fibrillated rayon, semi-synthetic cellulose such as acetate or triacetate, thermoplastic hydrophobic chemical fibers, or thermoplastic hydrophobic chemical fibers subjected to a hydrophilic treatment. Typical examples of the thermoplastic hydrophobic chemical fibers include single fibers such as PE (polyethylene), PP (polypropylene), or PET (polyethylene terephthalate), fibers obtained through graft polymerization of polyethylene and polypropylene, and compound fibers having a structure such as a core-in-sheath structure.

To form a nonwoven fabric web, any one of a dry method (such as a carding method, a spunbond method, a melt-blown method, or an air-laying method) and a wet method can be used. Multiple methods from the dry method and the wet method may be combined. Other methods include thermal bonding, needle punching, chemical bonding, and the like. A method for forming the nonwoven fabric is not limited to the methods given above.

Alternatively, a spunlace formed into a sheet through hydroentangling can be used as the topsheet 10. In addition, as the topsheet 10, a nonwoven fabric having recesses and bumps on its top layer side, or an uneven nonwoven fabric having an uneven basis weight by air blow in web formation. Formation of recesses and bumps in a surface can make it less likely for body fluid to spread along the surface of the topsheet 10 before permeating the topsheet 10.

In the present embodiment, an absorbable sheet 21 may be placed on a clothing-contact-surface side of the absorber 30. The absorbable sheet 21 is an absorbable sheet that absorbs liquid, and is a tissue, for example. The backsheet 20 is placed on the clothing-contact-surface side of the absorbable sheet 21. The backsheet 20, may be a film mainly made of polyethylene, polypropylene, or the like, a breathable resin film, or a sheet obtained by bonding a breathable resin film to a nonwoven fabric such as a spunbond or a spunlace can be used. The backsheet 20 is preferably formed of a material which is so flexible as not to give a wearer uncomfortable feeling. For example, a film mainly formed of an low density polyethylene (LDPE) resin having a basis weight of 15 to 30 $g/m^2$ is preferably used as the backsheet 20 (the basis weight is a weight (g) per unit area and is also called a substance weight).

In the present embodiment, for example, the absorber 30 may be formed of one or a combination of pulp, chemical pulp, rayon, acetate, natural cotton, a polymer absorber, a fibrous polymer absorber, synthetic fibers, a foam, and the like. Preferably, the absorber 30 does not easily deform and has low chemical stimulation. For example, the absorber may comprise hydrophilic fibres, including one or a combination of cellulose such as ground pulp or cotton, regenerated cellulose such as rayon or fibrillated rayon, semi-synthetic cellulose such as acetate or triacetate, a granular polymer, a fibrous polymer, thermoplastic hydrophobic chemical fibers, or thermoplastic hydrophobic chemical fibers subjected to a hydrophilic treatment.

Among these, the ground pulp is preferably used, considering its low cost and workability of forming an absorber. What is obtained by mixing a polymer absorber in hydrophilic fibers can be used as the absorber 30. In the present embodiment, a polymer absorber is a granular polymer, such as a sodium acrylate copolymer, having absorbability and moisture absorbability.

The absorber 30 may be an air-laid sheet obtained by forming hydrophilic fibers or powders into a sheet using an air-laying method. If an air-laid sheet is used as the absorber 30, the air-laid sheet preferably has a thickness of 0.3 mm to 5.0 mm. Examples of the air-laid sheet include what is obtained by shaping fibers and a granular polymer into a sheet product using a binder or the like. Note that, in the air-laid sheet, the granular polymer may spread in a layered manner, or may be concentrated in a thickness direction.

The absorber 30 may be formed of a single layer, or multiple absorber layers. In addition, a sheet, such as a tissue, a cushion sheet, or a diffusion sheet, may be interposed between the topsheet 10 and the absorber 30.

In the particular embodiment illustrated, a sanitary napkin, paired wing portions 40 are formed in the center area A of the absorbent article 1. The wing portions 40 protrude outward in a width direction of the absorbent article 1. The absorbent article 1 has a fixing area 60 on a surface of each of the paired wing portions 40, the surface being opposite to the wearer's skin side. The fixing area 60 is fixed onto the underwear of the wearer. In FIG. 1, the fixing areas 60 are shown in broken lines. The fixing areas 60 are provided with an adhesive, an adhesive tape, a hook-and-loop fastener, or the like. Moreover, an adhesive 70 (not shown in FIG. 1, see FIG. 2) is applied in multiple lines in the longitudinal direction L on a surface of the backsheet 20, the surface coming into contact with the underwear of the wearer. The paired wing portions 40 are folded back on a crotch portion of the underwear, and attached to the underwear by the adhesive applied on the fixing areas 60.

A hot-melt adhesive easily applicable in a desired pattern is used as the adhesive. The hot-melt adhesive is formed of a styrene polymer, a tackifier, and a plasticizer. As the styrene polymer, a styrene-ethylene-butylene-styrene block copolymer, a styrenebutadiene-styrene block copolymer, a styrene-isobutylene-styrene block copolymer, or the like can be used. In the present embodiment, a styrene-ethylene-butylene-styrene block copolymer is used. The adhesive is not limited to those given above. What can be used is a hot-melt adhesive which is pressure-sensitive at normal temperature, is soft, and can enter between fibers of the underwear at normal temperature and be attached thereto.

Figure 2:
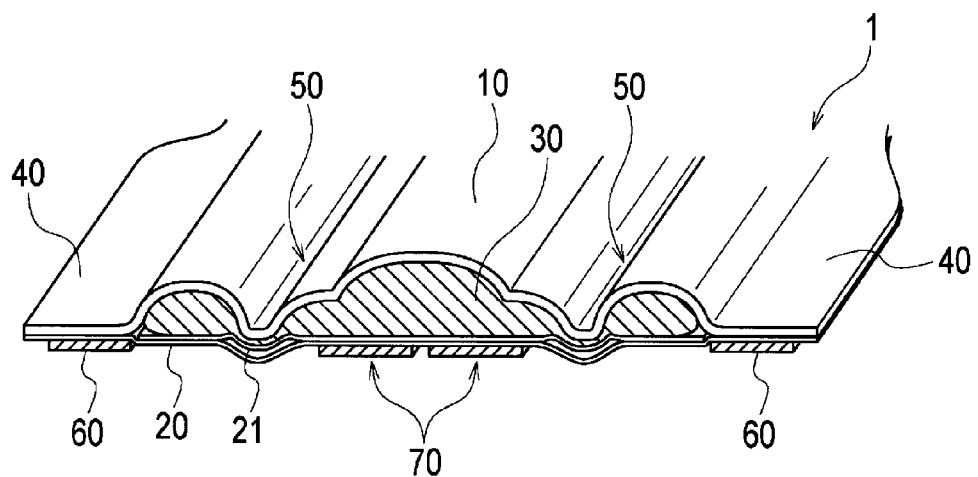
FIG. 2 is a perspective view including a cross section of the absorbent article taken along an X-X line in FIG. 1.

As FIGS. 1 and 2 show, a compressed portion 50 has been formed in the absorbent article 1 by compressing the absorber 30 in a compression process. Incidentally, FIG. 2 shows absorbent article 1 before a back-surface groove 52 is formed.

Figure 3:
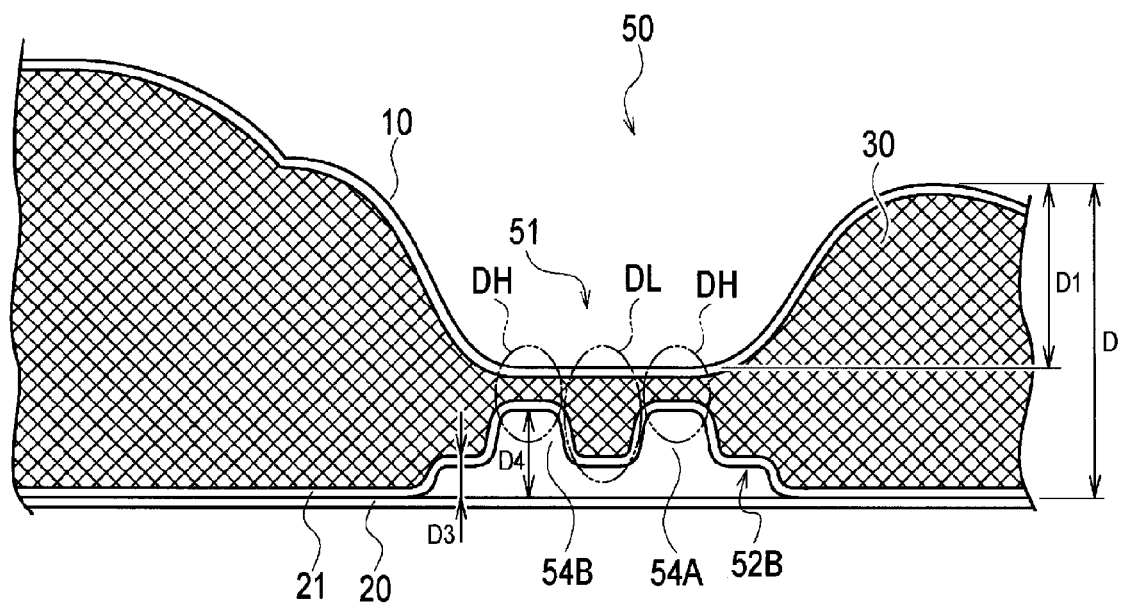
FIG. 3 is an enlarged view in which a compressed portion in the cross-sectional view of FIG. 2 is enlarged.

Hereinafter, the compressed portion 50 is described. FIG. 3 is an enlarged view of the compressed portion 50 in the cross-sectional view of FIG. 2. In a cross-sectional view of the absorbent article 1, the compressed portion 50 has a top-surface groove 51 formed on the skin-contact-surface side of the absorbent article 1, and the back-surface groove 52 formed on the clothing-contact-surface side of the absorbent article 1. The top-surface groove 51 is formed by depressing the topsheet 10 and the absorber 30 from the skin-contact-surface side to the clothing-contact-surface side. The back-surface groove 52 is formed on the clothing-contact-surface side of the top-surface groove 51 by depressing at least the absorber 30 from the clothing-contact-surface side to the skin-contact-surface side.

In the illustrated embodiments, the top surface groove 51 and back surface groove 52 are continuous, endless groves which extend around a region in which a liquid discharge is in use likely to occur. However, the invention may be applied to non continuous and/or non endless grooves, where a top surface groove and corresponding back surface groove border one side, or a portion of one side of where a discharge is likely to occur. In such arrangements, it may be preferable to apply two sets of such grooves, one to either side of the region of an absorbent article where a discharge is likely to occur.

In the embodiment of FIG. 3, an optional liquid absorbable sheet 21 is placed between the backsheet 20 and the absorber 30 and this is depressed into the back groove 52B and recessed portions 54A and 54B. The liquid impermeable back sheet is not so depressed and extends across the back groove 52, by being applied after the back groove 52b and recessed portions 54A and 54B have been formed.

Referring again to FIG. 3, in a bottom portion 52B of the back-surface groove 52, recessed portions 54A and 54B are formed. The recessed portions 54A and 54B are depressed from the bottom portion 52B of the back-surface groove 52 towards the skin-contact-surface side. A bottom portion 51B of the top-surface groove 51 is flatter than the bottom portion 52B of the back-surface groove 52. This structure allows a thick liquid to permeate into the top-surface groove 51 more easily than does a conventional structure in which small grooves are formed in the groove, in other words, than a hypothetical structure where the recessed portions 54A and 54B are formed on the topsheet 10 side. A thick liquid can permeate into the top-surface groove 51 easily because the bottom portion 51B of the top-surface groove 51 have no recessed portion narrower than the width of the top-surface groove 51. In the present embodiment, the bottom portion 51B of the top-surface groove 51 is almost flat. Note that being "almost" flat includes, for example, a surface formed by being pressed against a die subjected to a planarization process.

Moreover, since the recessed portions 54A and 54B are formed in the bottom portion 52B of the back-surface groove 52, the absorber 30 has a higher density at a portion positioned between the bottom portion 51B of the top-surface groove 51 and each of the recessed portions 54A and 54B of the back-surface groove 52 than at a portion positioned between the bottom portion 51B of the top-surface groove 51 and the bottom portion 52B of the back-surface groove 52. For this reason, in the bottom portion 51B of the top-surface groove 51, a compression part DL where the density of the absorber 30 is increased and high compression parts DH where the density of the absorber 30 is increased more than in the compression part DL are formed. Thus, the absorbability in the bottom portion 51B of the top-surface groove 51 is improved.

The top-surface groove 51 and the back-surface groove 52 are formed by being sandwiched by two rolls. The absorbable sheet 21 is placed on the clothing-contact-surface side of the absorber 30, and the back-surface groove 52 is formed by being pressed by one of the rolls from the wearers clothing-contact-surface side of the absorbable sheet 21, whilst the top surface groove 52 is formed by being pressed from the clothing contact side by the other roll. After the recessed portions 54A and 54B are formed by the roll, the clothing-contact-surface side of the absorbent article 1 is covered with the liquid impermeable backsheet 20. How to form the compressed portion 50 will be described later in detail.

A depth D1 of the top-surface groove 51 is preferably 20% to 80% of a pre-groove-formation thickness D of the absorbent article 1. It is more preferable that the depth D1 of the top-surface groove 51 be 30% to 60% of the thickness D of the absorbent article 1, considering how a liquid such as a menstrual blood flows, and improvement of deformability of the absorbent article 1 at the compressed portion 50.

In addition, a depth D3 of the back-surface groove 52 of the back-surface groove 52 each is 5% to 20% of the pre-groove-formation thickness D of the absorbent article 1. Further, the depth D3 of the back-surface groove 52 from the backsheet 20 is preferably smaller than a depth D4 of the recessed portions 54A and 54B. If the depth D3 of the back-surface groove 52 is less than 5% of the thickness D of the absorbent article 1, the absorbent article 1 has poor flexibility and does not easily deform by being bent at the compressed portion 50. Moreover, it is not preferable to set the depth D3 of the back-surface groove 52 to more than 20% of the thickness D of the absorbent article 1 because the absorbent article 1 becomes fragile.

As an example, suppose that the thickness D of the absorbent article 1 is 7 mm. In this case, it is preferable to set the depth D3 of the back-surface groove 52 to 0.4 mm and to set the depth D4 of the recessed portions 54A and 54B to 0.8 mm.

Figure 4:
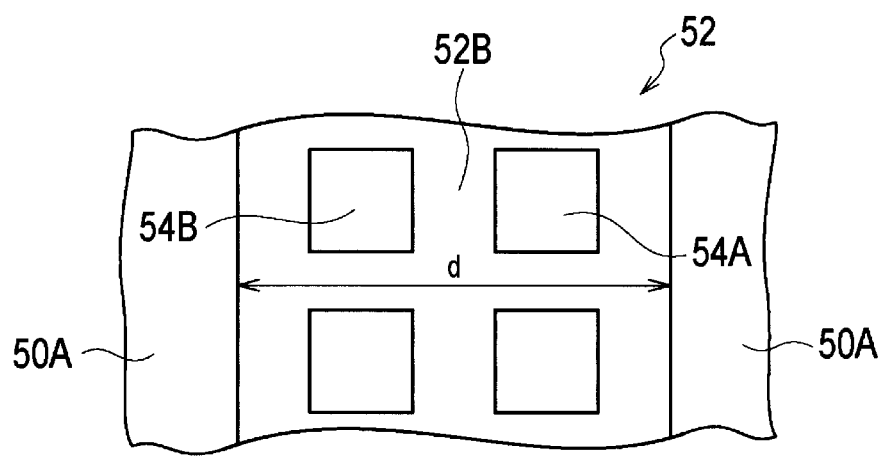
FIG. 4 is a plan view illustrating recessed portions formed in a back-surface groove of the absorbent article according to the embodiment present invention.

Next, a description is given of a pattern of the recessed portions 54A and 54B formed in the back-surface groove 52. FIG. 4 is a plan view enlarging a part around the back-surface groove 52. The recessed portions 54A and 54B are rectangular in a plan view seen from the clothing-contact-surface side of the absorbent article 1. The length of the diagonal line or the long side of the rectangle is smaller than a width d of the back-surface groove 52. As an example, multiple recessed portions 54A and multiple recessed portions 54B are formed in the bottom portion 52B of the back-surface groove 52, along the longitudinal direction L of the absorbent article 1.

Figure 5:
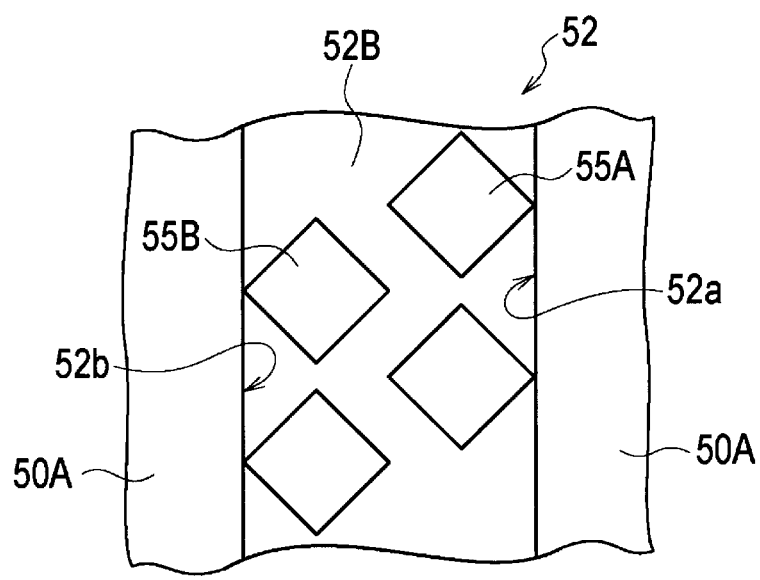
FIG. 5 is a plane view illustrating a different pattern of the recessed portions formed in the back-surface groove.

FIG. 5 is a plane view showing a different pattern of recessed portions formed in the bottom portion 52B of the back-surface groove 52. In the example shown in FIG. 5, recessed portions 55A and 55B are formed in the bottom portion 52B of the back-surface groove 52. As FIG. 5 shows, the bottom portion 52B of the back-surface groove 52 has the recessed portions 55A positioned closer to a border portion 52a between the back-surface groove 52 and an uncompressed portion 50A, and the recessed portions 55B positioned closer to a border portion 52b between the back-surface groove 52 and the uncompressed portion 50A. In FIG. 5, the recessed portions 55A and 55B are formed in a staggered manner. In the plan view of the back-surface groove 52 seen from the clothing-contact-surface side, the recessed portions 55A and 55B may be partially in contact with the respective border portions 52a and 52b between the back-surface groove 52 and the uncompressed portion 50A.

Figure 6:
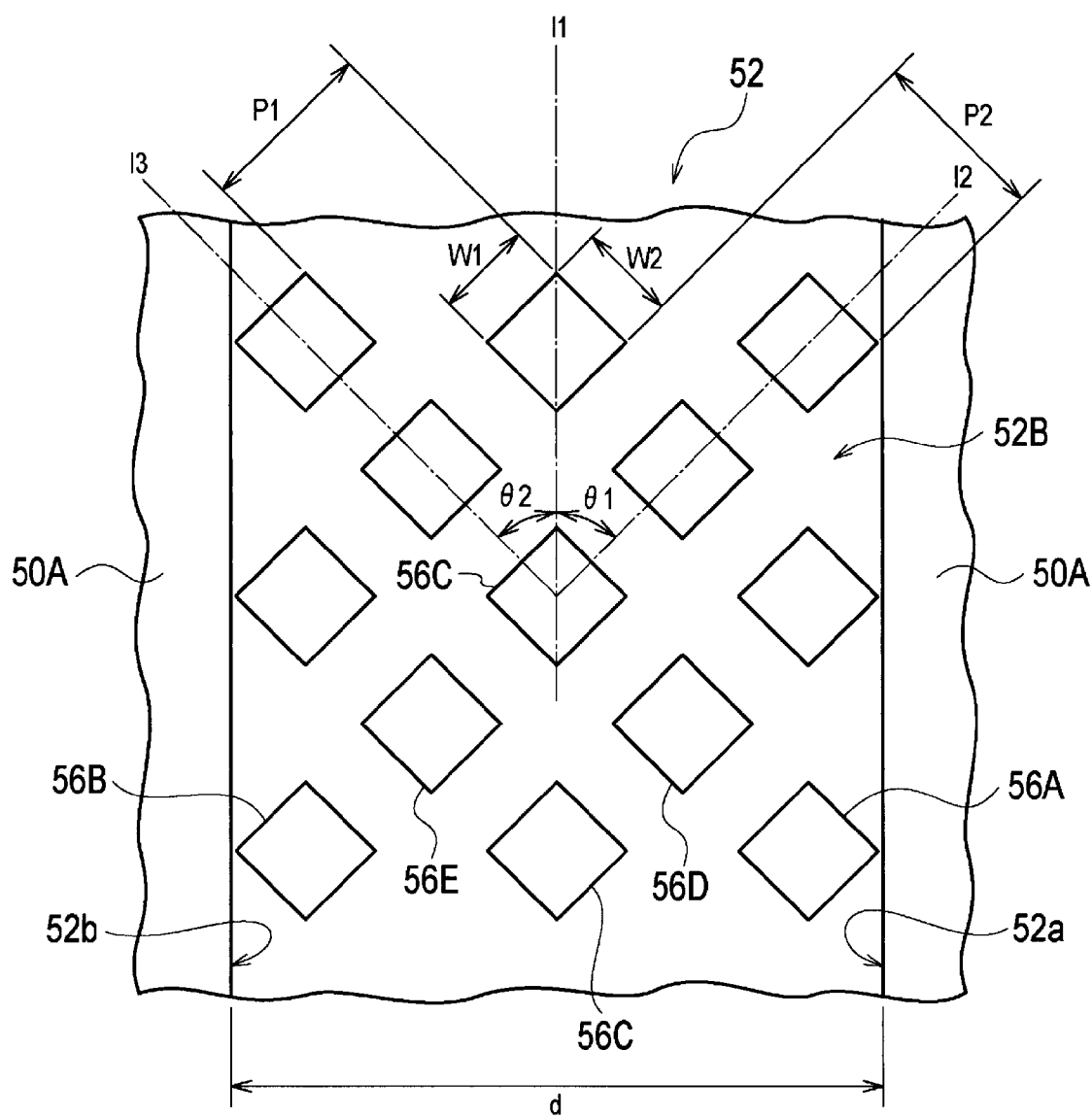
FIG. 6 is a plan view illustrating a yet different pattern of the recessed portions formed in the back-surface groove.

FIG. 6 is a plan view showing a yet different pattern of recessed portions formed in the bottom portion 52B of the back-surface groove 52. In the example shown in FIG. 6, recessed portions 56A, 56B, 56C, 56D, and 56E are formed in the back-surface groove 52. As FIG. 6 shows, the back-surface groove 52 has the recessed portions 56A positioned closer to the border portion 52a between the back-surface groove 52 and the uncompressed portion 50A, and the recessed portions 56B positioned closer to the border portion 52b between the back-surface groove 52 and the uncompressed portion 50A. In addition, the back-surface groove 52 has the recessed portions 56C between the recessed portions 56A and 56B.

The recessed portions 56D are formed between the recessed portions 56A and the recessed portions 56C. The recessed portions 56E are formed between the recessed portions 56B and the recessed portions 56C. The recessed portions 56A and the recessed portions 56D are formed in a staggered manner. Further, the recessed portions 56B and the recessed portions 56E are formed in a staggered manner. The recessed portions 56C are formed along a center line 11 of the back-surface groove 52.

For example, in the example shown in FIG. 6, each of the recessed portions is formed in a rhombus (square). More precisely, sides W1 and W2 of the recessed portion are each 0.8 mm. A pitch P1 of adjacent recessed portions adjacent in a direction perpendicular to one side of the concave portions is 1.6 mm, and a pitch P2 of concave portions adjacent in a direction perpendicular to another side of the recessed portions not facing the one side is 1.6 mm. Therefore, the area of each recessed portion is 0.64 mm2. Further, an angle theta1 formed by the center line 11 and a hypothetical line 12 perpendicular to the side W2 of each recessed portion 56C is 45 degrees. Moreover, an angle theta2 between the center line 11 and a hypothetical line 13 perpendicular to the side W1 of each recessed portion 56C is 45 degrees.

In forming the pattern in FIG. 6 in the topsheet 10 and the absorber 30 of the absorbent article 1, it is preferable that the area, on an absorbing surface, covered by the top-surface groove 51 be 0.5 $mm^2$ to 10 $mm^2$, and that the width d of the top-surface groove 51 be 0.5 mm to 3 mm.

It is generally known that an absorber is more likely to absorb liquid at an area having a high density. In the absorbent article 1 of the present invention, the bottom portion 51B of the top-surface groove 51 is formed almost flat, while in the bottom portion 52B of the back-surface groove 52, the recessed portions 54A and 54B depressed to the topsheet 10 side are formed. Accordingly, even though the bottom portion 51B of the top-surface groove 51 is almost flat, the compression part DL having a density higher than that in the uncompressed portion 50A and the high compression parts DH having a density still higher than that in the compression part DL are formed. The absorbent article 1 thus has a structure having a groove width which facilitates entrance of a thick liquid and having improved absorbability. Accordingly, the absorbent article 1 can speedily absorb a thick liquid at the high compression parts DH and the compression part DL. This can prevent leak caused when a thin body liquid spreads along the absorbing surface while the top-surface groove is clogged by a thick liquid.

Further, the absorbent article 1 has a structure in which the density of the absorber 30 increases in a stepwise manner on the back-surface side. More specifically, the compression part DL and the high compression parts DH are formed by forming the recessed portions 54A and 54B in the bottom portion 52B of the back-surface groove 52. This can prevent the topsheet from being damaged by excessive compression.

Moreover, by adopting the pattern shown in FIG. 5 or 6 of the recessed portions formed in the compressed portion 50, many recessed portions from which liquids can be more easily absorbed are arrangeable in a limited area of the groove. Thereby, an amount of liquid that can be absorbed at once increases. The absorbability of the absorbent article 1 can thus be improved.

In the present embodiment, only the topsheet 10 is placed on the skin-contact-surface side of the absorber 30. This causes a liquid having permeated the topsheet 10 to directly come into contact with pulp, hydrophilic fibers, a polymer absorber, or the like forming the absorber 30, thereby increasing the speed at which the liquid is absorbed. As described, liquid absorbability can be further improved by forming the recessed portions 54 on the clothing-contact-surface side of the absorbent article 1 and by not providing the absorbable sheet 21 on the skin-contact-surface side. Thereby, a liquid leak can be securely prevented.

Effects of the present embodiment have been described above mainly using the back-surface groove 52 and the recessed portions 54A and 54B shown in FIGS. 3 and 4, but the same effects are obtained with the recessed portion patterns shown in FIGS. 5 and 6.

Figure 7:
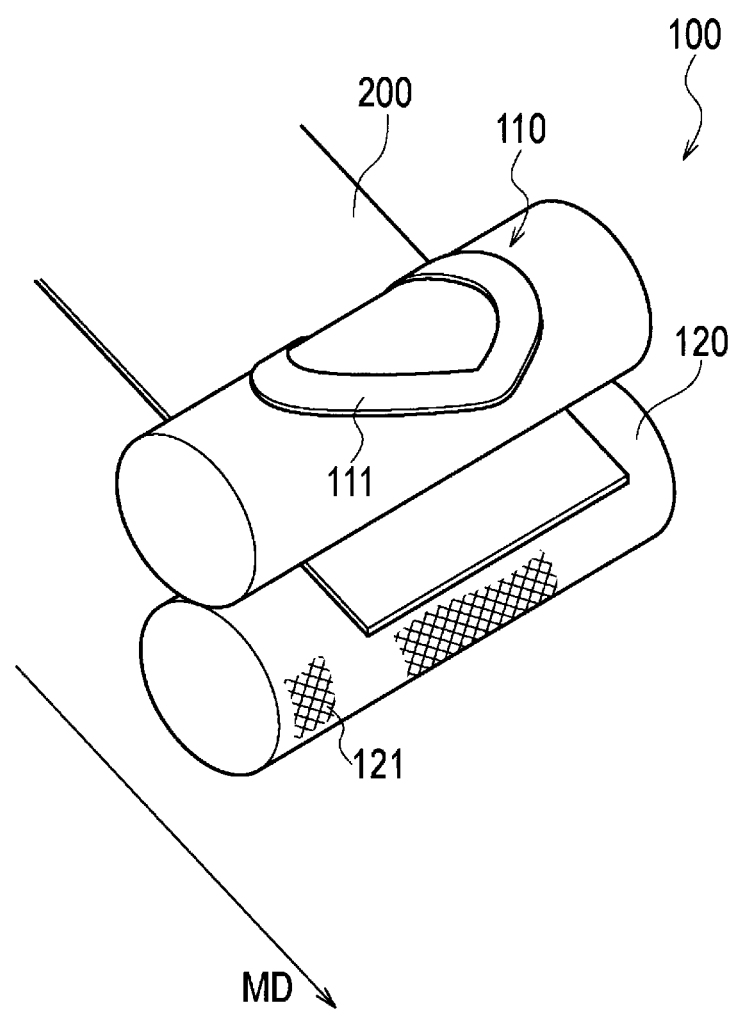
FIG. 7 is a schematic diagram of an apparatus that forms the back-surface groove and the recessed portions.

Next, how to form the above-described compressed portion 50 is described. FIG. 7 is a schematic diagram illustrating an apparatus for forming the compressed portion 50. As FIG. 7 shows, an apparatus 100 has a first roll 110 and a second roll 120.

While coming into contact with an intermediate continuum 200 obtained by stacking the absorber 30 on a topsheet continuum, the first roll 110 rotates in such a manner as to feed the intermediate continuum 200 in a machine direction MD which is a direction of flow of steps for manufacturing the absorbent article 1. The first roll 110 has a top-surface-groove die 111 against which back-surface-groove bump portions 121 formed on the surface of the second roll 120 are pressed with the intermediate continuum 200 in between. The second roll 120 will be described later. The top-surface-groove die 111 projects in a direction normal to the first roll 110, and its surface to come into contact with the intermediate continuum 200 has been subjected to a planarization process.

The multiple back-surface-groove bump portions 121 are formed on the surface of the second roll 120. The second roll 120 is placed facing the first roll 110 with the intermediate continuum 200 in between, and rotates in the machine direction MD. The back-surface-groove bump portions 121 are formed in a region in a surface of the second roll 120, including an area facing the top-surface-groove die 111. On the backsheet 20 side of the top-surface groove 51 of the intermediate continuum 200, the back-surface-groove bump portions 121 form the back-surface groove 52 depressed to the topsheet 10 side. The surface area of the region, in the second roll 120, where the back-surface-groove bump portions 121 are formed is larger than the surface area of the smooth surface of the top-surface-groove die 111.

The intermediate continuum 200 is fed in the machine direction MD while being nipped and pressed between the first roll 110 and the second roll 120. At this time, the intermediate continuum 200 is pressed against the surface of the second roll 120 by the top-surface-groove die 111 of the first roll 110. Thereby, shapes having a reverse pattern of the back-surface-groove bump portions 121 formed on the second roll 120 are formed on an area corresponding to the shape of the top-surface-groove die 111 of the intermediate continuum 200. More specifically, in the absorber 30 of the intermediate continuum 200, the back-surface groove 52 is formed, and the recessed portions 54A and 54B are formed in the bottom portion 52B of the back-surface groove 52.

As described above, the surface of the first roll 110 to come into contact with the intermediate continuum 200 only has the large die groove pattern on it and this is relatively smooth compared to the second roll 120 with both the back surface die groove and die recessed portions on it. Thereby the risk of damage to the topsheet of the intermediate continuum 200 is reduced and this can prevent breakage of the topsheet due to excessive pressing.

In previous arrangements, a bumpy pattern is sometimes formed on the surface of the die formed on the first roll. In such a case, however, not only is it difficult to form the bumpy pattern on the surface of the die of the first roll through a grinding process, but the die might be chipped since load tends to act on the indented die thus formed.

In contrast, in the present embodiment, since the recessed portions 54A and 54B are formed in the bottom portion 52B of the back-surface groove 52, a die for forming the back groove and recessed portions 54A and 54B is formed on the surface of the second roll 120. Accordingly, compared to the previous case where the recessed portions and bump portions are formed in the surface of the die of a roll, troubles such as chipping of the die can be prevented, and the durability of the roll can be improved. Furthermore, the manufacture can be speeded up. The productivity thus improves.

(Evaluation Test)

Figure 8:
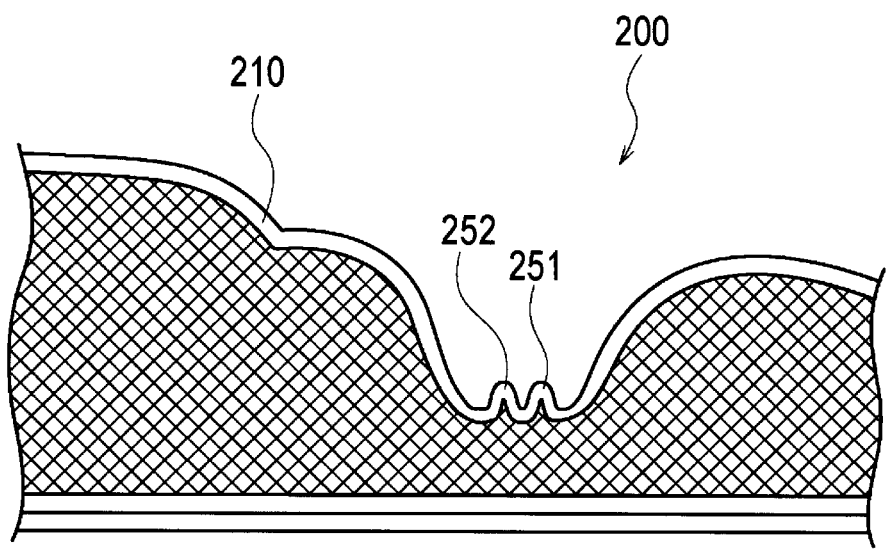
FIG. 8 is a cross-sectional view of a groove of a conventional absorbent article.

Absorbent articles in accordance with the tables below were used for an evaluation test. Sample 1 (conventional product): The topsheet is a polyethylene sheet. Sample 2 (Example 1 of the present invention 1): The topsheet is a polyethylene sheet. Sample 3 (conventional product): The topsheet is a nonwoven fabric sheet. Sample 4 (Example 2 of the present invention): The topsheet is a nonwoven fabric sheet. FIG. 8 shows an example of a conventional absorbent article. In a conventional absorbent article 200, a top-surface groove 250 is formed on the topsheet 210 side. Bump portions 251 and 252 are formed on the bottom portion of the top-surface groove 250.

The absorbent articles of the present invention and the conventional absorbent articles were compared in terms of absorbability. 2 ml of artificial menstrual blood was dropped on a compressed area formed on the absorbing surface of each absorbent article, and the distance that the artificial menstrual blood has spread along the compressed area was measured after a predetermined period (30 seconds). After another 30 seconds, 2 ml of artificial menstrual blood was dropped, and the distance that the artificial menstrual blood has spread along the compressed area was measured.

What was used as the artificial menstrual blood was a liquid obtained by adding 80 g of glycerin, 8 g of carboxymethylcellulose sodium, 10 g of sodium chloride, 4 g of sodium hydrogen carbonate, 8 g of Red Dye No. 102, 2 g of Red Dye No. 2, and 2 g of Yellow Dye No. 5 to 1 L of ion-exchanged water.

Four tests were conducted on each sample, and a mean value was obtained. The results are shown in Table 1.

TABLE 1

| | Number of Tests | Dropped Blood | |
|---|---|---|---|
| | | 1st. Time(mm) | 2st. Time(mm) |
| Sample 1 | 1 | 8.86 | 13.42 |
| | 2 | 7.52 | 12.23 |
| | 3 | 7.17 | 11.41 |
| | 4 | 8.63 | 11.23 |
| | ave. | 8.05 | 12.07 |
| Sample 2 | 1 | 5.76 | 11.19 |
| | 2 | 4.74 | 7.78 |
| | 3 | 6.33 | 9.68 |
| | 4 | 5.04 | 7.28 |
| | ave. | 5.47 | 8.98 |
| Sample 3 | 1 | 13.58 | 19.41 |
| | 2 | 17.52 | 21.26 |
| | 3 | 13.77 | 19.04 |
| | 4 | 14.39 | 19.04 |
| | ave. | 14.82 | 19.69 |
| Sample 4 | 1 | 8.2 | 14.86 |
| | 2 | 9.39 | 13.85 |
| | 3 | 10.23 | 15.87 |
| | 4 | 12.34 | 16.54 |
| | ave. | 10.04 | 15.28 |

It can be seen from the above measurement results that: between Sample 1 and Sample 2 in which a nonwoven fabric sheet was used as the topsheet, the artificial menstrual blood spread less in Sample 2; and between Sample 3 and Sample 4 in which a polyethylene sheet was used as the topsheet, the artificial menstrual blood spread less in Sample 4. Spreading less means that the artificial menstrual blood was absorbed by the absorber before streaming along the topsheet. Accordingly, it can be seen from the results of Sample 2 and 4 that even when the topsheet of the same material is used, an absorbent article has more improved absorbability when the recesses of the bottom portion of the back-surface groove formed on the wear's clothing side are larger than the recesses of the bottom portion of the top-surface groove formed on the topsheet side.

Other Embodiments

As described above, the details of the present invention have been disclosed by using the embodiment of the present invention. However, it should be understood that the description and drawings which constitute part of this disclosure do not limit the present invention. From this disclosure, various alternative embodiments, examples, and operation techniques will be easily found by those skilled in the art.

For example, the embodiment of the present invention has described a case where the absorbent article is a sanitary napkin, but the present invention is not limited to this case, and may be applied to a diaper, an inner liner, a urine collection pad, or the like.

The shape of the recessed portions 54A and 54B formed in the compressed portion 50 is not limited to the shape shown in FIGS. 4 to 6. For example, the recessed portions 54A and 54B may be circular, oval, and the like. In addition, the border portions between the top-surface groove 51 and the uncompressed portion and between the back-surface groove 52 and the uncompressed portion do not have to be straight, and may be, for example, a curved line such as a wavy line.

The above embodiment has described a case where, in the back-surface groove 52, the absorbable sheet 21 and the absorber 30 are depressed towards the topsheet 10 side, and the backsheet 20 is placed on the clothing side of the absorbable sheet 21. Although it is preferable to provide the absorbable sheet 21 in consideration of manufacture handleability in forming a groove in the absorber 30, the absorbable sheet 21 does not have to be provided. Moreover, although the above embodiment has described a case where only the topsheet 10 is placed on the wear's skin side, the absorbable sheet 21 may be interposed between the topsheet 10 and the absorber 30.

How to form the compressed portion 50 is not limited to using the above-described apparatus 100 in FIG. 7. Further, in forming the compressed portion 50, the temperature of the rolls, the distance (space) between the rolls, and the rotation speed of the rolls can be appropriately adjusted.

The surface area of the back-surface-groove dierecess portions 121 formed on the second roll 120 only has to be larger than the surface area of the smooth surface of the top-surface-groove die 111.

As described above, the present invention naturally includes various embodiments which are not described herein. Accordingly, the technical scope of the present invention should be determined only by the matters to define the invention in the scope of claims regarded as appropriate based on the description.

Note that the entire contents of the Japanese Patent Application No. 2009-229093, filed on Sep. 30, 2009 is incorporated herein by reference.

Further, the aspects of the present invention may be arranged described in at least the following items. In the absorbent article, at least one of the first recessed portions or the second recessed portions is in contact with the respective side edge portion of the back-surface groove.

In the absorbent article, the absorbent sheet may be depressed in the back-surface groove together with the absorber toward the skin-facing side. In the absorbent article, the bottom portion of the top-surface groove may be substantially flat.

In the absorbent article, a depth of the top-surface groove may be 20% to 80% of a thickness of a uncompressed portion of the absorber. In the absorbent article, a depth of the back-surface groove may be 5% to 20% of a thickness of a uncompressed portion of the absorber.

In the manufacturing apparatus, the top-surface-groove die may have a flat surface. In the manufacturing apparatus, the back-surface-groove bump portions may include first bump portions for forming first recessed portions adjacent one of side edge portions of the back-surface groove, and second bump portions for forming second recessed portions adjacent an opposite one of the side edge portions of the back-surface groove.

Further, in the manufacturing apparatus, the first and second bump portions are arranged such that the first recessed portions and the second recessed portions are arranged in a staggered manner. In the manufacturing apparatus, at least one of the first bump portions or the second bump portions is arranged such that at least one of the first recessed portions or the second recessed portions is in contact with the respective side edge portion of the back-surface groove.

The invention claimed is:

1. An absorbent article comprising:
    a liquid permeable topsheet;
    a liquid impermeable sheet;
    an absorber interposed between the topsheet and the liquid impermeable sheet and configured to absorb liquid;
    a top-surface groove formed in a predetermined area of the top surface in which the topsheet and the absorber are depressed towards a clothing-contact-surface side; and
    a back-surface groove formed in the clothing-contact-surface side in register with the top-surface groove in which at least the absorber is depressed towards a skin-contact-surface side, wherein
    in a widthwise cross section of the absorbent article,
    a recessed portion is formed in a bottom portion of the back-surface groove, the recessed portion recessed from the bottom portion of the back-surface groove towards the skin-contact-surface side, and
    the absorber has a higher density at a portion between the bottom portion of the top-surface groove and the recessed portion of the back-surface groove than at a portion between the bottom portion of the top-surface groove and the bottom portion of the back-surface groove.

2. An absorbent article as claimed in claim 1, wherein a bottom portion of the top-surface groove is flatter than the bottom portion of the back-surface groove.

3. The absorbent article according to claim 1, wherein in a plan view of the absorbent article,
    a plurality of recessed portions are formed and arranged along a longitudinal direction of the back-surface groove, and include first recessed portions in contact with one of side edge portions of the back-surface groove and second recessed portions in contact with an opposite one of the side edge portions of the back-surface groove, and
    the first recessed portions and the second recessed portions are arranged in a staggered manner.

4. The absorbent article according to claim 1, further comprising an absorbable sheet configured to absorb liquid, wherein
    the absorbable sheet is interposed between the absorber and the liquid impermeable sheet, and
    only the topsheet is placed on the skin-contact-surface side of the absorber.

5. The absorbent article according to claim 1 wherein the liquid impervious sheet is a backsheet of the absorbent article.

6. The absorbent article according to claim 5 wherein the backsheet extends flat across the back surface groove.

7. The absorbent article according to claim 1 wherein the top groove is an endless groove.

8. The absorbent article of claim 1 in the form of a sanitary napkin.

9. A manufacturing apparatus for an absorbent article including a liquid permeable topsheet, a liquid impermeable sheet, and an absorber interposed between the topsheet and the liquid impermeable sheet and configured to absorb liquid, the manufacturing apparatus being configured to form a groove in a predetermined area of the topsheet of the absorbent article, and comprising:
    a first roll configured to rotate in a machine direction which is a direction of flow of steps for manufacturing the absorbent article, while being in contact with an intermediate continuum obtained by stacking the absorber on a continuum of the topsheet;

a second roll placed facing the first roll with the intermediate continuum in between and configured to rotate in the machine direction, and apparatus for applying the liquid permeable sheet to the intermediate continuum after the top surface groove, back surface groove and recess have been formed in the intermediate continuum, wherein a top-surface-groove die is formed on a surface of the first roll, the top-surface-groove die being configured to form a top-surface groove in a predetermined area of the intermediate continuum, the top-surface groove being depressed from the topsheet, a back surface groove die, and a plurality of back-surface-groove bump portions are formed on a surface of the second roll in an area including a region facing the top-surface-groove die, the back-surface-groove bump portions being configured to form a back surface groove depressed toward the topsheet in an area of the intermediate continuum on a side having the liquid impermeable sheet, the area corresponding to the top-surface groove.

10. A manufacturing apparatus as claimed in claim 9, wherein the top surface groove die has a flat surface, and a surface area of the back surface groove die in the second roll is larger than a surface area of the flat surface of the top-surface-groove die.

\* \* \* \* \*